United States Patent
Folsom, Jr.

(10) Patent No.: US 8,057,230 B1
(45) Date of Patent: Nov. 15, 2011

(54) CERAMIC AND METAL COMPOSITE DENTAL IMPLANT

(76) Inventor: Aubrey C. Folsom, Jr., Pelham, AL (US)

( * ) Notice: Subject to any disclaimer, the term of this patent is extended or adjusted under 35 U.S.C. 154(b) by 706 days.

(21) Appl. No.: 12/034,007

(22) Filed: Feb. 20, 2008

(51) Int. Cl.
*A61C 8/00* (2006.01)

(52) U.S. Cl. ........................................ 433/174

(58) Field of Classification Search .......... 433/172–176, 433/201.1; 623/17.17, 23.44, 17.18, 16.11
See application file for complete search history.

(56) References Cited

U.S. PATENT DOCUMENTS

| | | | |
|---|---|---|---|
| 4,259,072 A | 3/1981 | Hirabayashi et al. | |
| 4,483,678 A | 11/1984 | Nishio et al. | |
| 4,531,915 A | 7/1985 | Tatum | |
| 4,960,381 A | 10/1990 | Niznic | |
| 5,015,186 A | 5/1991 | Detsch | |
| 5,152,687 A | 10/1992 | Amino | |
| 5,205,745 A | 4/1993 | Kamiya et al. | |
| 5,564,924 A | 10/1996 | Kwan | |
| 5,571,016 A | 11/1996 | Ingber et al. | |
| 5,636,989 A | 6/1997 | Somborac et al. | |
| 5,685,714 A | 11/1997 | Beaty et al. | |
| 6,012,923 A * | 1/2000 | Bassett et al. | 433/172 |
| 6,419,491 B1 | 7/2002 | Ricci et al. | |
| 6,755,651 B2 | 6/2004 | Brodbeck | |
| D511,833 S | 11/2005 | Wohrle | |
| 2001/0018176 A1* | 8/2001 | Branemark | 433/173 |
| 2003/0120279 A1* | 6/2003 | Hansson | 606/73 |
| 2004/0234925 A1 | 11/2004 | Benhamou | |

* cited by examiner

*Primary Examiner* — Sunil K Singh
(74) *Attorney, Agent, or Firm* — Kenneth M. Bush; Bush Intellectual Property Law

(57) ABSTRACT

A dental implant having a hollow ceramic cylinder compressed between two metal components of the implant. A principal embodiment comprises a hollow ceramic cylinder, a hollow abutment with an anti-rotational feature, a metallic tip with a hollow metal core, and a screw. The metal core is press-fit into the ceramic cylinder providing a metallic tip at the apical or bottom end of the ceramic cylinder. The screw is inserted into the hollow abutment and extends into and screws into the metal core. By tightening the screw, the ceramic cylinder can be compressed to improve its strength, and the abutment is thereby reversibly attached to the hollow ceramic cylinder. The hollow ceramic cylinder is implantable in both bone and soft tissue, extends through the interface between the bone and soft tissue, maintains the normal appearance of gum tissue after implantation, and has a maximum diameter between 1.8 to 6 mm.

8 Claims, 5 Drawing Sheets

CERAMIC AND METAL COMPOSITE DENTAL IMPLANT

FIELD OF THE INVENTION

The present invention relates to tissue implants used to support prosthetic devices and, more particularly, to a dental implant comprising a compressed ceramic material to maintain the normal appearance of gum tissue and increase the tensile strength of the implant.

BACKGROUND OF THE INVENTION

Dental implants generally consist of an implant which is anchored within bone, and an abutment that is connected to the implant to support a prosthesis, such as a prosthetic tooth or denture. The abutment partially extends into the oral cavity in the position of the tooth it is to replace. The majority of dental implants are made of metal, usually titanium. Metal implants are easily threaded internally for attachment of prosthetic abutments. A problem with metal implants is that the coronal region of a metal implant shows through gum tissue as a dark shadow, thus making the prosthetic tooth look unnatural and unhealthy.

Ceramic implants are light in color, translucent, and appear more like natural tooth roots, thus avoiding the dark shadow found with metal implants. Gingival tissues typically attach quicker and more securely to ceramic than to titanium, thus providing a better seal around the neck of the implant. This improves the overall health of the implant site, for example, by avoiding infection and thus reducing the likelihood of implant rejection. However, there are a number of problems associated with ceramic implants. For example, dental implants are subjected to very high forces from mastication of food and, as a result, ceramic implants have a history of breakage due to their lack of tensile strength. Further, ceramic implants are typically manufactured as one-piece constructs of the implant and the abutment and, as a result, these implants are difficult to restore if the angulations or location of the surgical placement deviate from ideal.

Titanium dental implants with a ceramic sleeve cemented in the coronal region are known. There are several disadvantages to this design. If the ceramic sleeve is thin, it is fragile and the dark opaque metal of the implant shows through the gum making it appear less natural. If the ceramic sleeve is made thicker to overcome the problems with the thin ceramic sleeve, the implant diameter becomes too large for the implant site.

What is needed, and is not found in the prior art, is a dental implant that comprises both metal and ceramic to maximize the benefits of these two materials while avoiding the inherent weaknesses of the ceramic material.

SUMMARY OF THE INVENTION

The present invention is a composite dental implant having a hollow ceramic cylinder compressed between two metal components of the implant. In a preferred embodiment, the ceramic cylinder has a metal core inserted therein, wherein the metal core is threaded internally on one end so an abutment or prosthesis can be affixed to the implant with a screw. The metal core is placed in tension by tightening the screw used to attach the prosthesis. The metallic core can be fabricated to have a tip portion that shoulders against the apical end of the ceramic cylinder. This tip portion of the core may be extended in the apical direction and threaded externally to engage bone. The metal tip can be threaded with sharper and more widely spaced threads than the ceramic, thus adding to initial stability of the implant during the healing phase.

The tension in the metal core places the ceramic cylinder in compression. The compressive strengths of most ceramic products are seven to ten times greater than their respective tensile strengths. If ceramic structural members are placed in compression, they are capable of carrying much larger loads than members without this compression. Through application of this principle of compression, tensile stresses are avoided, providing marked improvement in resistance to failure from both static and impact loadings on ceramic cylinders.

The composite implant with its ceramic cylinder and metal tip can be implanted into bone and gum tissue and the bone and gum tissue allowed to heal and attach to the implant. After healing, an abutment can be attached to the implant with a screw. A prosthetic tooth can then be attached to the abutment.

An advantage of the present invention is a ceramic dental implant that allows a portion of the ceramic implant to be placed in the gum tissue, promoting adherence of the gum tissue to the implant and allowing the gum tissue to retain its normal appearance.

Another advantage is the added strength of compressed ceramic which allows a smaller diameter implant to be constructed that will match the size of the tooth root being replaced.

Another advantage is a dental implant with a metal tip that can be threaded with deep widely spaced threads to obtain initial stability in bone.

Another advantage is a dental implant with a metal tip that will integrate with the surrounding bone.

Another advantage is a ceramic dental implant that can be implanted in bone and gum tissue and allowed to heal before attaching an abutment.

Other advantages and features of the invention will be described in the following detailed description of the preferred embodiments.

DETAILED DESCRIPTION OF THE PREFERRED EMBODIMENTS

Figure 1:
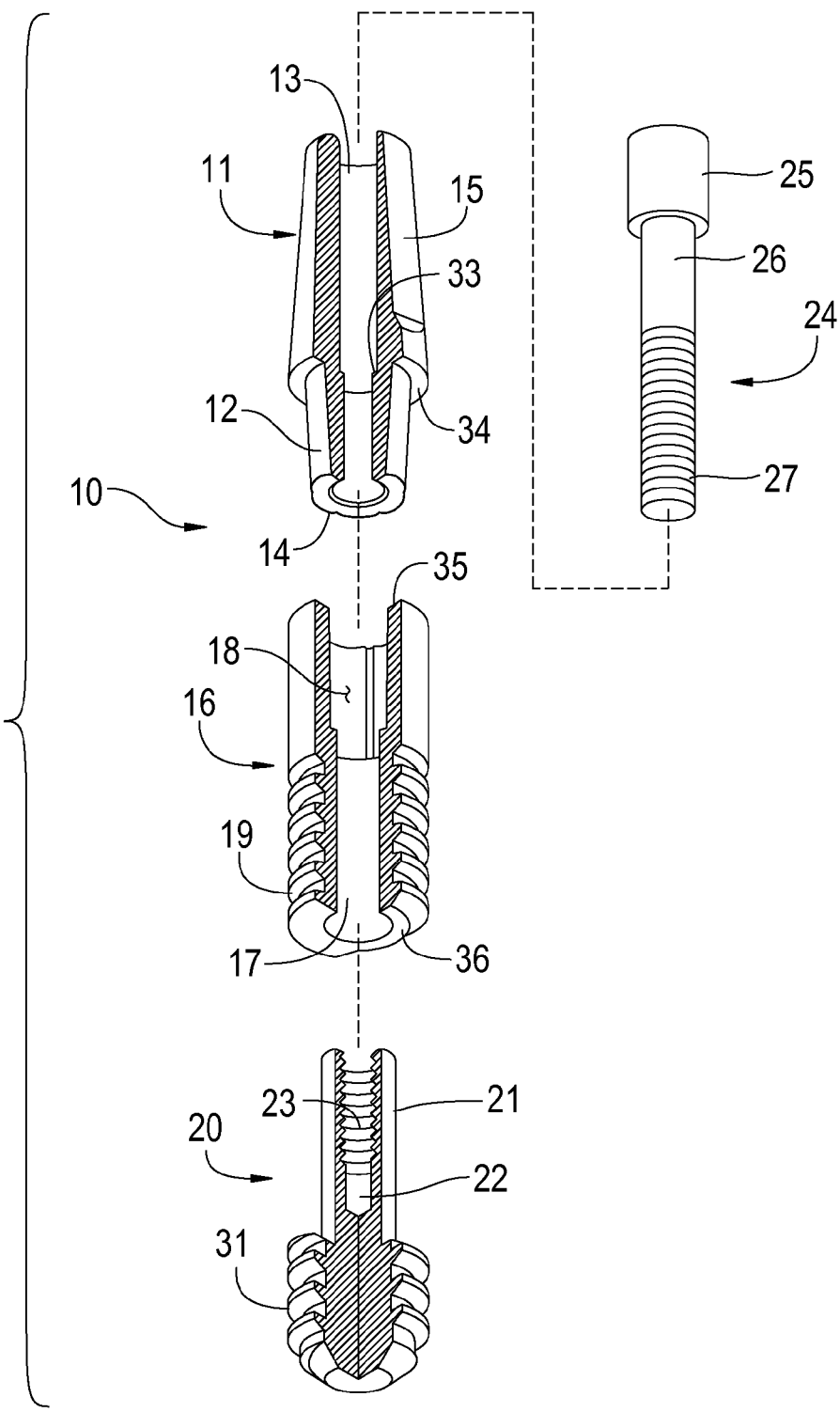
FIG. 1 is an exploded perspective view, partially in section, of the preferred embodiment of the present invention.
Figure 2:
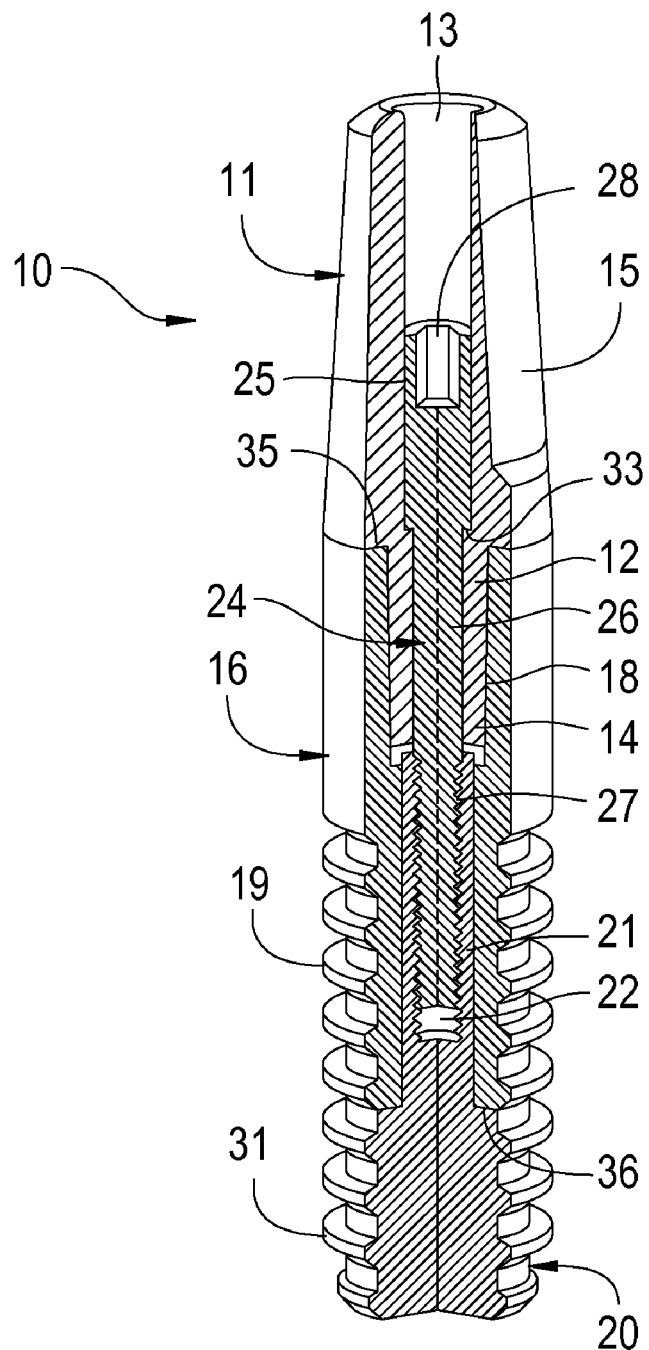
FIG. 2 is a perspective view, partially in section, of the assembled preferred embodiment of the present invention.
Figure 3:
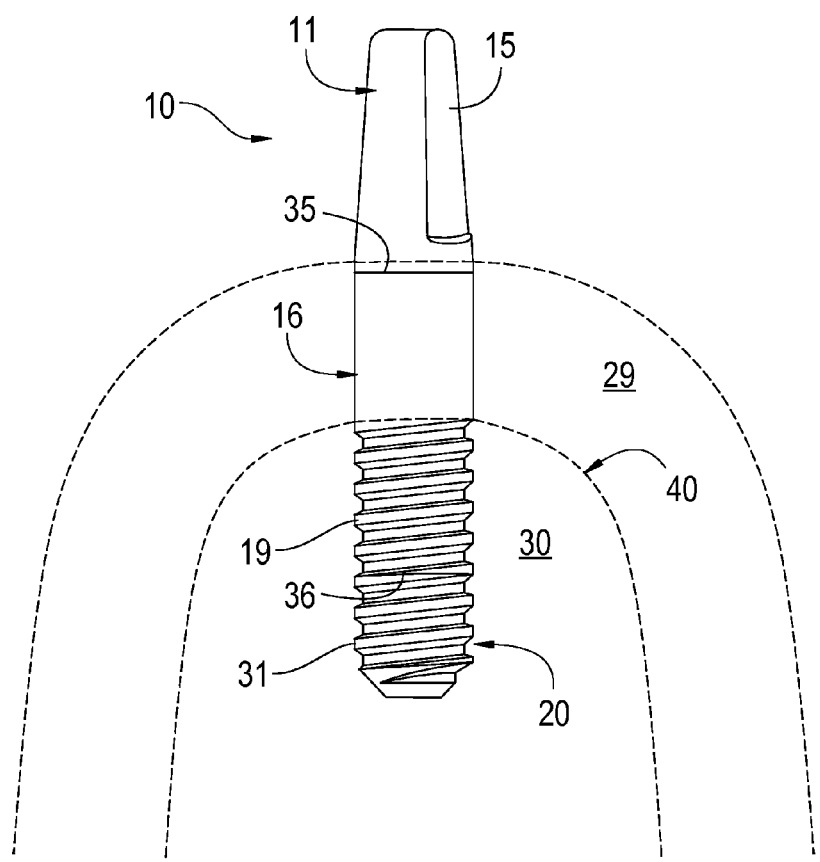
FIG. 3 is an illustrative view of the invention implanted in bone and gum tissue.

The preferred embodiment of the present invention is shown in FIGS. 1-3, wherein FIG. 1 is an exploded perspective view, partially in section, of the invention showing the components of the composite dental implant 10. An abutment 11 has a hollow interior 13, an exterior shelf 34, and an anti-rotational feature 12. The internal diameter of the anti-rotational feature 12 is slightly less than that of the abutment 11, producing an interior shelf 33. The anti-rotational feature 12 has convex protrusions 14 on its exterior surface. The abutment 11 may be made of ceramic or metal, such as titanium or gold.

The composite dental implant 10 has a hollow ceramic cylinder 16 having an interior cavity 17, a bottom (apical) end 36 and a top (coronal) end 35. The internal upper portion of hollow ceramic cylinder 16 has concave depressions 18 on its inner surface to engage the external convex protrusions 14 of the anti-rotational feature 12. Hollow ceramic cylinder 16 has external grooves or threads 19 near its bottom end 36 to promote oseointegration in bone, and has a smooth external surface near its top end 35 to promote attachment of gum tissue. The ceramic of ceramic cylinder 16 preferably comprises zirconium oxide or aluminum oxide A metal tip 20, preferably made of titanium, is attached to the bottom end 36 of hollow ceramic cylinder 16 by means of a hollow metal core 21 extending from metal tip 20. Metal core 21 is insertable a fixed distance through the bottom end 36 of hollow ceramic cylinder 16, and is press-fit within its hollow interior cavity 17. Metal core 21 has a hollow interior 22 with threads 23 on its internal surface. Metal tip 20 has external grooves or threads 31 to promote stability in bone.

A screw 24, preferably made of titanium, is used to attach abutment 11 to ceramic cylinder 16 and metal tip 20. Screw 24 has a head 25 and a small diameter shaft 26. Shaft 26 has threads 27 constructed to engage threads 23 in the interior of metal core 21.

FIG. 2 is a perspective view, partially in section, of the assembled dental implant 10. Anti-rotational feature 12 of abutment 11 is reversibly insertable a fixed distance into the top end 35 of hollow ceramic cylinder 16. The convex projections 14 on anti-rotational feature 12 engage the concave depressions 18 on the inner surface near the top end 35 of hollow ceramic cylinder 16 so that abutment 11 cannot rotate relative to hollow ceramic cylinder 16. As the exterior shelf 34 of abutment 11 contacts upper end 35 of hollow ceramic cylinder 16, anti-rotational feature 12 cannot extend further into ceramic cylinder 16.

Screw 24 is inserted into abutment 11 and extended into anti-rotational feature 12 and into metal core 21 of metal tip 20. Screw 24 can be threaded into metal core 21 as threads 27 of shaft 26 engage threads 23 of metal core 21. Head 25 of screw 24 contacts interior shelf 33 of abutment 11, and head 25 cannot extend into anti-rotational feature 12. When head 25 contacts interior shelf 33 additional torque applied to head 25 produces a tensile force in metal core 21. This tensile load or force places the hollow ceramic cylinder 16 in compression. This compressive force strengthens hollow ceramic cylinder 16 and provides an increased durability of this ceramic component 16. Screw head 25 has an open end 28 for the application of a tool so that the tool can rotate and apply torque to screw 24, as is known in the art.

FIG. 3 shows the composite dental implant 10 in position in bone 30 and gum tissue 29. In a preferred application, the threaded portions 31, 19 of metal tip 20 and hollow ceramic cylinder 16 are placed in bone tissue 30. The smooth or non-grooved portion (the coronal portion) of hollow ceramic cylinder 16 extends into gum or soft tissue 29. The hollow ceramic cylinder 16 with its metal tip 20 can remain in this position until healing occurs, as bone tissue 30 grows into the threaded portions 31 and 19, and as gum tissue attaches to the coronal non-threaded portion of hollow ceramic cylinder 16. Hollow ceramic cylinder 16 extends from bone 30, through the interface 40 between bone 30 and gum 29, and into the gum tissue 29. Abutment 11 can then be reversibly inserted into the top end 35 of hollow ceramic cylinder 16. Abutment 11 can have a flat portion 15 to prevent rotation of a prosthetic tooth and to locate the prosthetic tooth. Screw 24 can be inserted into abutment 11, anti-rotational feature 12, and metal core 21, and tightened with as much force as desired to produce an effective compression of hollow ceramic cylinder 16, and to reversibly attach abutment 11 onto hollow ceramic cylinder 16.

Because of the construction of the composite dental implant 10 of the present invention it is possible to have a strong and durable dental implant with a maximum diameter of about 1.8-6 mm, preferably about 4 mm. In addition, the coronal upper aspect of the hollow ceramic cylinder 16 in the gum tissue 29 has no dark metal or shadow showing through the ceramic material. Thus, the gum tissue 29 retains its normal healthy appearance when the composite ceramic implant 10 is implanted in bone and gum tissue.

Figure 4:
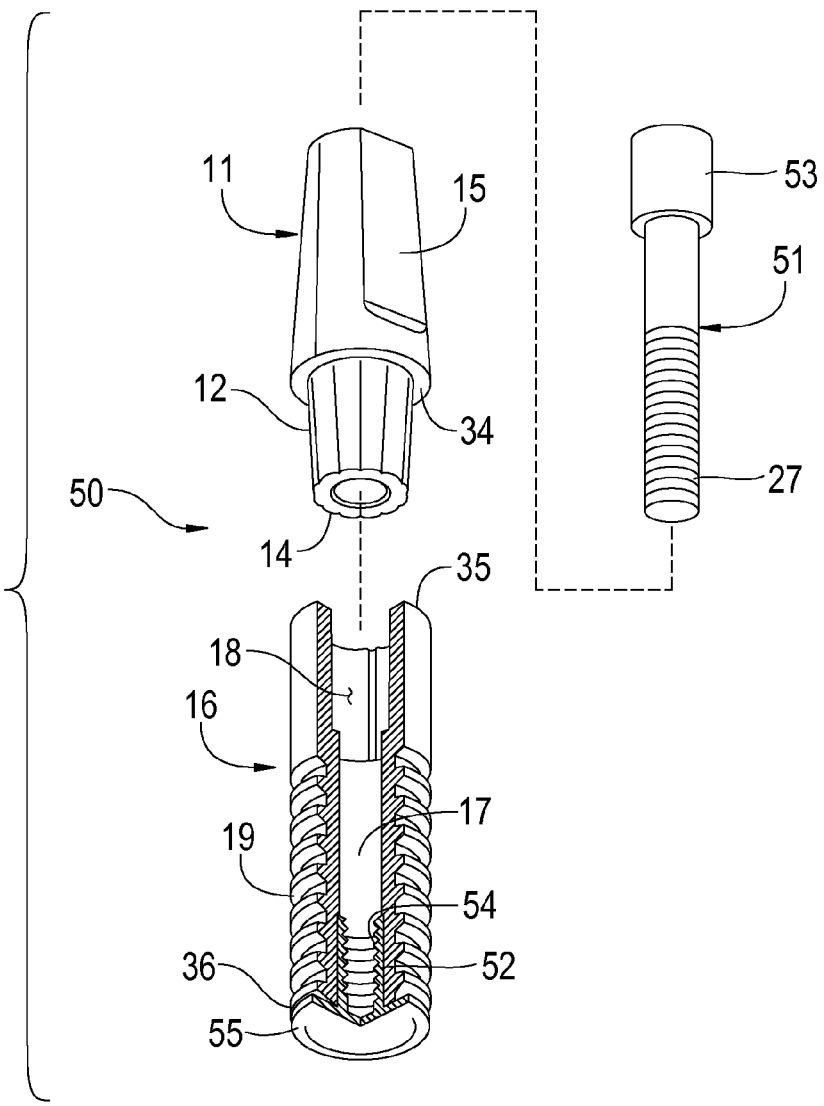
FIG. 4 is an exploded perspective view, partially in section, of an alternate embodiment of the present invention.

FIG. 4 is an exploded perspective view, partially in section, of an alternate embodiment of the present invention. The composite dental implant 50 has an abutment 11 with an anti-rotational feature 12 and a hollow ceramic cylinder 16 similar to those shown in FIGS. 1-3. At the bottom end 36 of hollow ceramic cylinder 16 within internal cavity 17 is a metal core 52, preferably made of titanium, having a head 55 and internal threads 54. Metal core 52 may be press-fit into the bottom end 36 of hollow ceramic cylinder 16 and secured thereto with an adhesive. Screw 51, preferably made of titanium, is inserted into abutment 11 and extended into anti-rotational feature 12, into ceramic hollow cylinder 16, and into the threaded metal core 52. Screw 51 can be screwed into the threaded metal core 52. Head 53 of screw 51 contacts an interior shelf in abutment 11, similar to that shown in FIG. 2, and head 53 cannot extend into anti-rotational feature 12. As the exterior shelf 34 of abutment 11 contacts the top end 35 of hollow ceramic cylinder 16, anti-rotational feature 12 cannot extend further into hollow ceramic cylinder 16. When head 53 contacts the interior shelf in abutment 11, additional torque applied to head 53 to rotate screw 51 into metal core 52 produces a tensile load in screw 51 and metal core 52. This tensile load places the hollow ceramic cylinder 16 in compression, strengthening and increasing the durability of this ceramic component.

Figure 5:
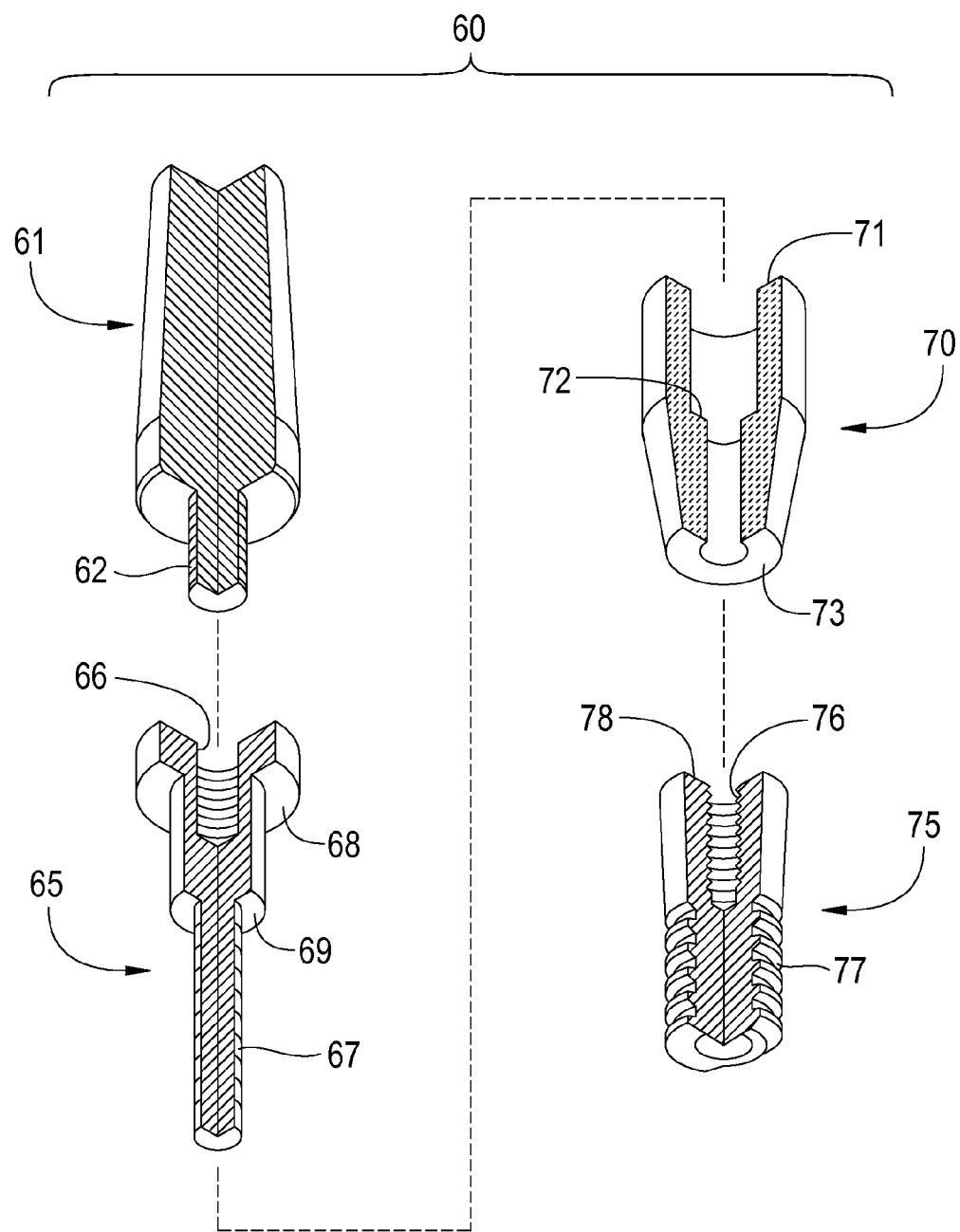
FIG. 5 is an exploded perspective view, partially in section, of another alternate embodiment of the present invention.

FIG. 5 is an exploded perspective view, partially in section, of another alternate embodiment of the present invention. The composite dental implant 60 has an abutment 61 with a lower extension 62 having exterior threads, an upper metal member 65, preferably made of titanium, having an upper channel 66 having internal threads and a lower extension 67 having exterior threads, a hollow ceramic cylinder 70, and a lower metal member 75, preferably made of titanium, having an upper channel 76 having internal threads and a lower portion 77 having exterior threads. In use, the upper metal member 65 is inserted though the ceramic cylinder 70 and the lower extension 67 of the upper metal member 65 is screwed into the upper channel 76 of the lower metal member 75. As the lower extension 67 is screwed into the upper channel 76, an upper shelf 68 of the upper metal member 65 engages the top surface 71 of the ceramic cylinder 70, a lower shelf 69 of the upper metal member 65 preferably engages an inner shelf 72 of the ceramic cylinder 70, and a bottom surface 73 of the ceramic cylinder 70 engages the top surface 78 of the lower metal member 75. Additional torque applied to the upper metal member 65 to rotate the lower extension 67 into the upper channel 76 produces a tensile load in the upper metal member 65 and the lower metal member 75. This tensile load places the ceramic cylinder 70 in compression, strengthening and increasing the durability of this ceramic component. The implant portion comprising the upper metal member 65, the ceramic cylinder 70, and the lower metal member 75 is then inserted into the jaw, after which, the lower extension 62 of the abutment 61 is screwed into the upper channel 66 of the upper metal member 65.

It is to be understood that various changes in the details, materials, and arrangements of the parts, which have been described and illustrated above in order to explain the nature of this invention, may be made by those skilled in the art without departing from the principle and scope of the invention as described herein and as recited in the appended claims. For example, the abutments can be made from any ceramic, metal, or plastic material. Also, the compression members used to place the ceramic cylinder in compression can be made from any suitable metal and can also be made of plastic, ceramic, carbon fibers, glass fibers, or a combination thereof. The composite dental implant can be implanted anywhere in the upper jaw bone or lower jaw bone. Further, the composite implant may be used in other medical applications, such as in other tissue or orthopedic implant applications. The screws can be made of any suitable metal or plastic. The abutment can be fashioned in any desired shape, and can engage the ceramic cylinder externally as well as internally by methods well known in the art.

The invention claimed is:

1. A dental implant, comprising:
   a) a ceramic cylinder comprising an internal channel therethrough, a top end, a bottom end, an internal surface, and an external surface, wherein said external surface of said ceramic cylinder has a lower threaded end for insertion into bone tissue, wherein said lower threaded end is configured to directly contact the bone tissue when inserted into said bone tissue;
   b) an abutment comprising an internal channel therethrough, a top end, a bottom end, an internal surface, and an external surface, wherein a lower end of said abutment is insertable into said internal channel of said ceramic cylinder a distance through said top end of said ceramic cylinder;
   c) an implant tip comprising an elongated core having a threaded internal channel therein, wherein said core is insertable into said internal channel of said ceramic cylinder a fixed distance through said bottom end of said ceramic cylinder, wherein the implant tip further comprises an outer surface that is threaded for insertion into the bone tissue; and
   d) a screw comprising an elongated threaded shaft, wherein said screw is reversibly insertable through said internal channel of said abutment, through said internal channel of said ceramic cylinder, and into said internal channel of said core such that said threaded shaft engages said threaded internal channel of said core, wherein said screw is operable to produce compression of said ceramic cylinder when said threaded shaft of said screw is screwed into said threaded internal channel of said core while reversibly attaching said abutment to said ceramic cylinder;
   e) wherein said ceramic cylinder is implantable in both bone and soft tissue such that said ceramic cylinder extends through the interface between the bone and soft tissue.

2. A dental implant according to claim 1, wherein said abutment, said implant tip, and said screw are made of metal.

3. A dental implant according to claim 1, wherein said ceramic cylinder maintains the normal appearance of gum tissue after implantation.

4. A dental implant according to claim 1, wherein said ceramic cylinder has a maximum diameter between about 1.8 to 6 mm.

5. A dental implant, comprising:
   a) a ceramic cylinder comprising an internal channel therethrough, a top end, a bottom end, an internal surface, and an external surface, wherein said external surface of said ceramic cylinder has a lower threaded end for insertion into bone tissue, wherein said lower threaded end is configured to directly contact the bone tissue when inserted into said bone tissue;
   b) an abutment comprising an internal channel therethrough, a top end, a bottom end, an internal surface, and an external surface, wherein a lower end of said abutment is insertable into said internal channel of said ceramic cylinder a fixed distance through said top end of said ceramic cylinder;
   c) an implant tip comprising an elongated core having a threaded internal channel therein, wherein said core is insertable into said internal channel of said ceramic cylinder a fixed distance through said bottom end of said ceramic cylinder, wherein the implant tip further comprises an outer surface that is threaded for insertion into the bone tissue; and
   d) a screw comprising an elongated threaded shaft, wherein said screw is reversibly insertable through said internal channel of said abutment, through said internal channel of said ceramic cylinder, and into said internal channel of said core such that said threaded shaft engages said threaded internal channel of said core, wherein said screw is operable to produce compression of said ceramic cylinder when said threaded shaft of said screw is screwed into said threaded internal channel of said core while reversibly attaching said abutment to said ceramic cylinder;
   e) wherein said ceramic cylinder is implantable in both bone and soft tissue such that said ceramic cylinder extends through the interface between the bone and soft tissue and maintains the normal appearance of gum tissue after implantation.

6. A dental implant according to claim 5, wherein said abutment, said implant tip, and said screw are made of metal.

7. A dental implant according to claim 5, wherein said ceramic cylinder has a maximum diameter between about 1.8 to 6 mm.

8. A dental implant, comprising:
   a) a ceramic cylinder comprising an internal channel therethrough, a top end, a bottom end, an internal surface, and an external surface, wherein said internal surface of said ceramic cylinder has an upper end having concave depressions and said external surface of said ceramic cylinder has a lower threaded end for insertion into bone tissue, wherein said lower threaded end is configured to directly contact the bone tissue when inserted into said bone tissue;
   b) a metal abutment comprising an internal channel therethrough, a top end, a bottom end, an internal surface, and an external surface, wherein said external surface of said abutment has a lower end having convex protrusions, wherein said lower end of said abutment is insertable into said internal channel of said ceramic cylinder a fixed distance through said top end of said ceramic cylinder, and wherein said convex protrusions of said abutment engage said concave depressions of said ceramic cylinder to prevent said abutment from rotating relative to said ceramic cylinder;
   c) a metal tip comprising an elongated metal core having a threaded internal channel therein, wherein said core is insertable into said internal channel of said ceramic cylinder a fixed distance through said bottom end of said ceramic cylinder, wherein the implant tip further comprises an outer surface that is threaded for insertion into the bone tissue; and
   d) a metal screw comprising an elongated threaded shaft, wherein said screw is reversibly insertable through said internal channel of said abutment, through said internal channel of said ceramic cylinder, and into said internal channel of said metal core such that said threaded shaft engages said threaded internal channel of said metal core, wherein said screw is operable to produce compression of said ceramic cylinder when said threaded shaft of said screw is screwed into said threaded internal channel of said metal core while reversibly attaching said abutment to said ceramic cylinder;

e) wherein said ceramic cylinder is implantable in both bone and soft tissue such that said ceramic cylinder extends through the interface between the bone and soft tissue, maintains the normal appearance of gum tissue after implantation, and has a maximum diameter between 1.8 to 6 mm.

* * * * *